United States Patent
Wang

(10) Patent No.: US 10,820,681 B2
(45) Date of Patent: Nov. 3, 2020

(54) COLOR REPRODUCTION SERVICES

(71) Applicant: Christina Wang, Los Angeles, CA (US)

(72) Inventor: Christina Wang, Los Angeles, CA (US)

(*) Notice: Subject to any disclaimer, the term of this patent is extended or adjusted under 35 U.S.C. 154(b) by 25 days.

(21) Appl. No.: 16/342,869

(22) PCT Filed: Oct. 18, 2017

(86) PCT No.: PCT/US2017/057232
§ 371 (c)(1),
(2) Date: Apr. 17, 2019

(87) PCT Pub. No.: WO2018/075666
PCT Pub. Date: Apr. 26, 2018

(65) Prior Publication Data
US 2019/0246773 A1 Aug. 15, 2019

Related U.S. Application Data

(60) Provisional application No. 62/501,219, filed on May 4, 2017, provisional application No. 62/409,714, filed on Oct. 18, 2016.

(51) Int. Cl.
*A45D 44/00* (2006.01)
*G06T 7/90* (2017.01)
*H04N 5/225* (2006.01)
*H04N 5/232* (2006.01)

(52) U.S. Cl.
CPC .............. *A45D 44/005* (2013.01); *G06T 7/90* (2017.01); *H04N 5/2256* (2013.01); *H04N 5/232* (2013.01); *A45D 2044/007* (2013.01); *G06T 2207/10024* (2013.01); *G06T 2207/10152* (2013.01); *G06T 2207/30201* (2013.01)

(58) Field of Classification Search
CPC .................... A45D 44/0005; A45D 2044/007; G06T 7/90; G06T 2207/10024; G06T 2207/10152; G06T 2207/30201; H04N 5/2256; H04N 5/232; A61B 5/441; A61K 8/00; A61K 8/18; A61K 2800/805; A61K 2800/882
See application file for complete search history.

(56) References Cited

U.S. PATENT DOCUMENTS

| | | | | |
|---|---|---|---|---|
| 5,622,692 A | * | 4/1997 | Rigg | A61B 5/442 356/402 |
| 6,052,195 A | * | 4/2000 | Mestha | G01J 3/46 250/226 |
| 6,177,093 B1 | * | 1/2001 | Lombardi | A61K 8/00 424/401 |
| 7,433,102 B2 | | 10/2008 | Takahashi et al. | |
| 9,498,974 B2 | * | 11/2016 | Choi | A45D 44/00 |
| 2011/0128362 A1 | * | 6/2011 | Shi | G06K 9/00255 348/77 |
| 2013/0293702 A1 | * | 11/2013 | Xin | G01J 3/0216 348/135 |

(Continued)

FOREIGN PATENT DOCUMENTS

WO 2015/191824 A2 12/2015

*Primary Examiner* — Dominic J Bologna
(74) *Attorney, Agent, or Firm* — Van Court & Aldridge LLP

(57) ABSTRACT

Systems, methods, and computer-readable media for a color reproduction service are provided.

20 Claims, 4 Drawing Sheets

(56) References Cited

U.S. PATENT DOCUMENTS

2014/0174595 A1   6/2014  Milhorn
2015/0181265 A1*  6/2015  Clavenna .............. H04L 65/605
                                                      348/159
2015/0360017 A1*  12/2015  Rabe ....................... B41J 3/407
                                                      604/290

* cited by examiner

300

400

COLOR REPRODUCTION SERVICES

CROSS-REFERENCE TO RELATED APPLICATIONS

This application is a National Phase entry of International Patent Application No. PCT/US2017/057232, filed Oct. 18, 2017, which claims the benefit of prior filed U.S. Provisional Patent Application No. 62/409,714, filed Oct. 18, 2016, and U.S. Provisional Patent Application No. 62/501,219, filed May 4, 2017, each of which is hereby incorporated by reference herein in its entirety.

TECHNICAL FIELD

This disclosure relates to color reproduction services, such as color discovery, color profiling, and color creation services and, more particularly, to systems, methods, and computer-readable media for discovering accurate relative color on a physical surface and rapidly reproducing that color in a substance on demand.

BACKGROUND OF THE DISCLOSURE

Color customization and accurate color reproduction have been fast growing areas of interest in numerous industries from home improvement to color cosmetics, especially in liquid makeup foundations for an increasingly diverse global population. Therefore, a need exists for self-serve color profiling and custom color creation.

SUMMARY OF THE DISCLOSURE

This document describes systems, methods, and computer-readable media for a color reproduction service.

For example, a method for defining a mixture is provided that may include capturing a photograph of a first base material using a first image capturing subsystem with first image capturing settings while the first base material is illuminated within a first space by a first light emitting subsystem with a first lighting setup, determining a color of the first base material using the captured photograph of the first base material, capturing a photograph of a second base material using a second image capturing subsystem with second image capturing settings while the second base material is illuminated within a second space by a second light emitting subsystem with a second lighting setup, determining a color of the second base material using the captured photograph of the second base material, wherein the determined color of the second base material is different than the determined color of the first base material capturing a photograph of a subject using a third image capturing subsystem with third image capturing settings while the subject is illuminated within a third space by a third light emitting subsystem with a third lighting setup, determining a color of the subject using the captured photograph of the subject, wherein the determined color of the subject is different than the determined color of the first base material, and wherein the determined color of the subject is different than the determined color of the second base material, and, using the determined color of the first base material and the determined color of the second base material and the determined color of the subject, determining a combination including a first amount of the first base material and a second amount of the second base material such that a color of the determined combination matches the determined color of the subject.

As another example, a system is provided that may include an image capturing ("IC") subsystem, a light emitting ("LE") subsystem, a light meter ("LM") subsystem, and a color reproduction service ("CRS") subsystem communicatively coupled to the IC subsystem and the LE subsystem and the LM subsystem and including a processor operative to capture an image of a first base material using the IC subsystem with first image capturing settings when the first base material is determined by the LM subsystem to be illuminated by the LE subsystem with a first lighting setup, determine a color of the first base material using the captured image of the first base material, capture an image of a second base material using the IC subsystem with the first image capturing settings when the second base material is determined by the LM subsystem to be illuminated by the LE subsystem with the first lighting setup, determine a color of the second base material using the captured image of the second base material, capture an image of a subject using the IC subsystem with the first image capturing settings when the subject is determined by the LM subsystem to be illuminated by the LE subsystem with the first lighting setup, determine a color of the subject using the captured image of the subject, and, based on the determined color of each one of the first base material, the second base material, and the subject, calculate a mixture including a first amount of the first base material and a second amount of the second base material such that a color of the calculated mixture is the same as the determined color of the subject.

As yet another example, a non-transitory computer-readable storage medium is storing at least one program is provided, where the at least one program includes instructions, which when executed by an electronic device, may cause the electronic device to obtain an image of a first base material, wherein the image of the first base material was captured using first image capturing settings while the first base material was illuminated with a first lighting setup, obtain an image of a second base material, wherein the image of the second base material was captured using first image capturing settings while the second base material was illuminated with the first lighting setup, obtain an image of a subject, wherein the image of the subject was captured using first image capturing settings while the subject was illuminated with the first lighting setup, determine a color of the first base material using the obtained image of the first base material, determine a color of the second base material using the obtained image of the second base material, determine a color of the subject using the obtained image of the subject, and calculate, using the determined color of each one of the first base material, the second base material, and the subject, a mixture including a first amount of the first base material and a second amount of the second base material such that a color of the calculated mixture is the same as the determined color of the subject.

This Summary is provided only to summarize some example embodiments, so as to provide a basic understanding of some aspects of the subject matter described in this document. Accordingly, it will be appreciated that the features described in this Summary are only examples and should not be construed to narrow the scope or spirit of the subject matter described herein in any way. Unless otherwise stated, features described in the context of one example may be combined or used with features described in the context of one or more other examples. Other features, aspects, and advantages of the subject matter described herein will become apparent from the following Detailed Description, Figures, and Claims.

BRIEF DESCRIPTION OF THE DRAWINGS

The discussion below makes reference to the following drawings, in which like reference characters may refer to like parts throughout, and in which.

DETAILED DESCRIPTION OF THE DISCLOSURE

A color reproduction service is provided that may be operative to detect a color of a subject and to reproduce that detected color with a single base material or a combination of different base materials. The service may first isolate a space from ambient light. Then, the service may use a consistently replicable lighting setup to illuminate a subject (e.g., a surface of a human face) within the space at a particular color temperature and intensity. With that lighting setup held constant, one or more photographs of the illuminated subject may be captured by any suitable image capturing device (e.g., a digital camera) that may be configured with one or more pre-determined image capturing device settings including, but not limited to, aperture, shutter speed, white balance (if present), ISO and/or ASA film speed, ISO and/or ASA film or image sensor sensitivity, and/or the like. The color of the subject may be determined from a particular pixel or from any suitable combination of pixels of the one or more photographs (e.g., averaged from a group of pixels (e.g., a pixel or group of pixels selected by a user or automatically by an application)). To translate this determined color of the subject to another reproduction material or substance (e.g., any suitable liquid, paint, powder, etc.), each one of various base materials of different colors may be photographed using the same replicable lighting setup and image capturing device settings as used for photographing the subject, and the color of each photographed base material may be determined in a similar fashion to the color determination of the photographed subject (e.g., by analyzing the color of a single photo pixel or by analyzing the average of colors over a number of photo pixels). The different determined colors of the various base materials may then be used in conjunction with the determined color of the subject to calculate which particular base material or which combination of which subset of base materials may combine together to recreate the determined color of the subject in that base material(s). Then, the calculated base material(s) may be mixed together and/or otherwise prepared and provided to a user (e.g., to the subject). Multiple photographs of the subject may be captured in succession by an image capturing device or by different image capturing devices, where each photograph may be captured with different image capturing device settings and/or with different lighting setups (e.g., different color temperatures and/or different intensities), to improve accuracy of the service when paired with corresponding multiple photographs of the one or more base materials.

Figure 1:
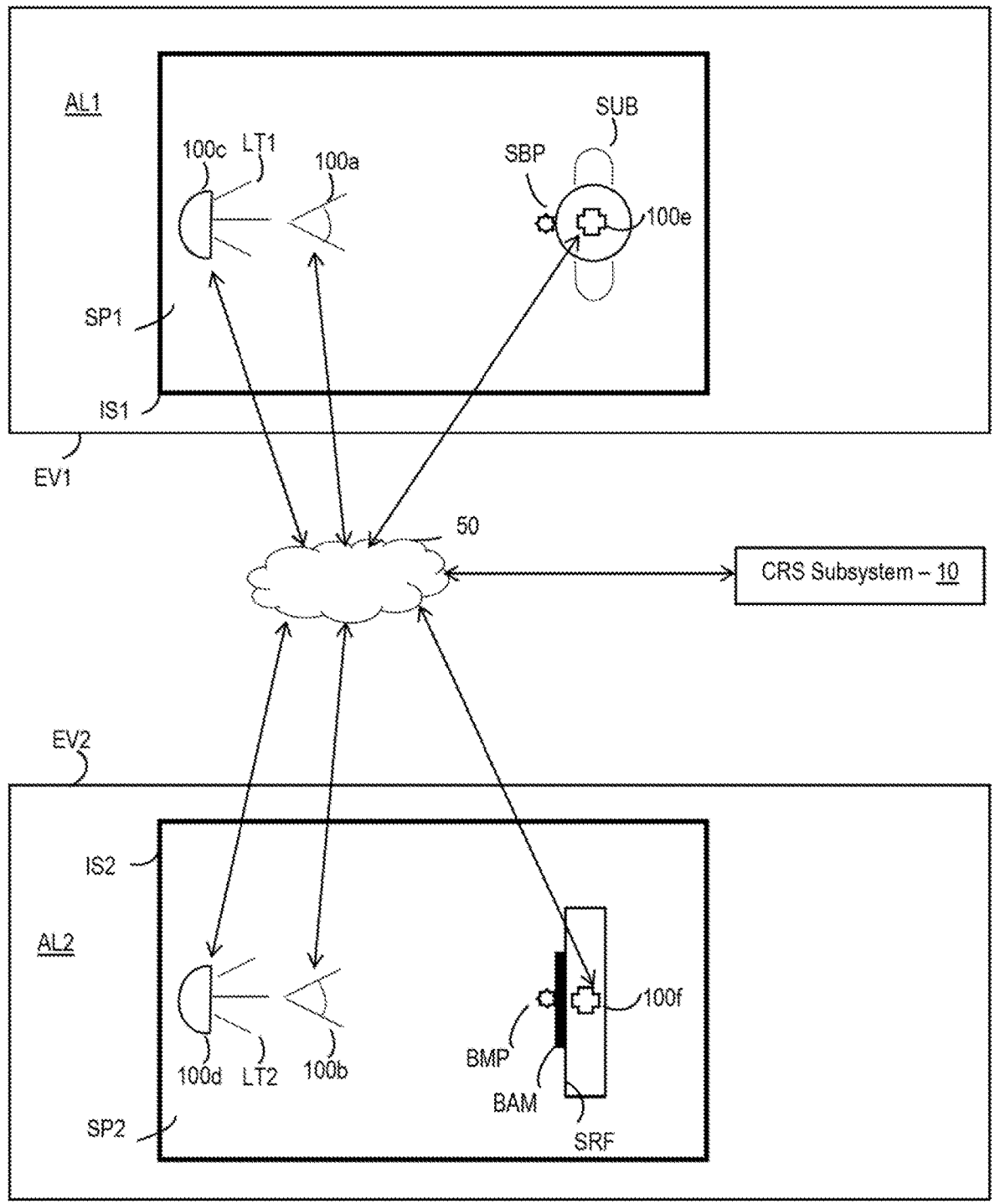
FIG. 1 is a schematic view of an illustrative system that may provide a color reproduction service of the disclosure.
Figure 1A:
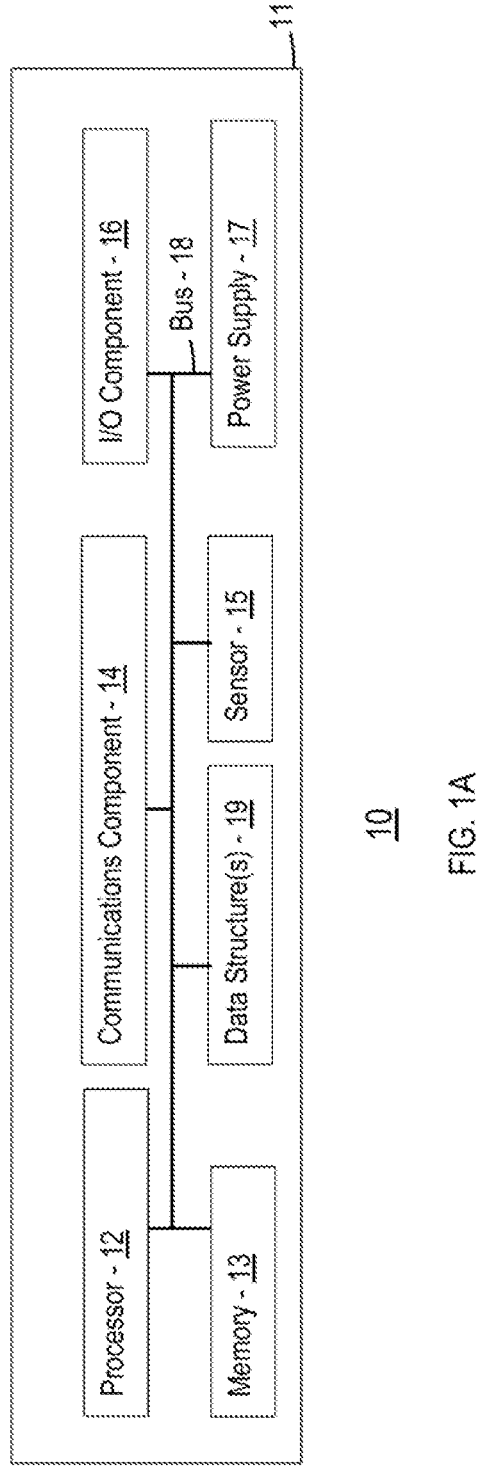
FIG. 1A is a more detailed schematic view of a subsystem of the system of FIG. 1.
Figure 2:
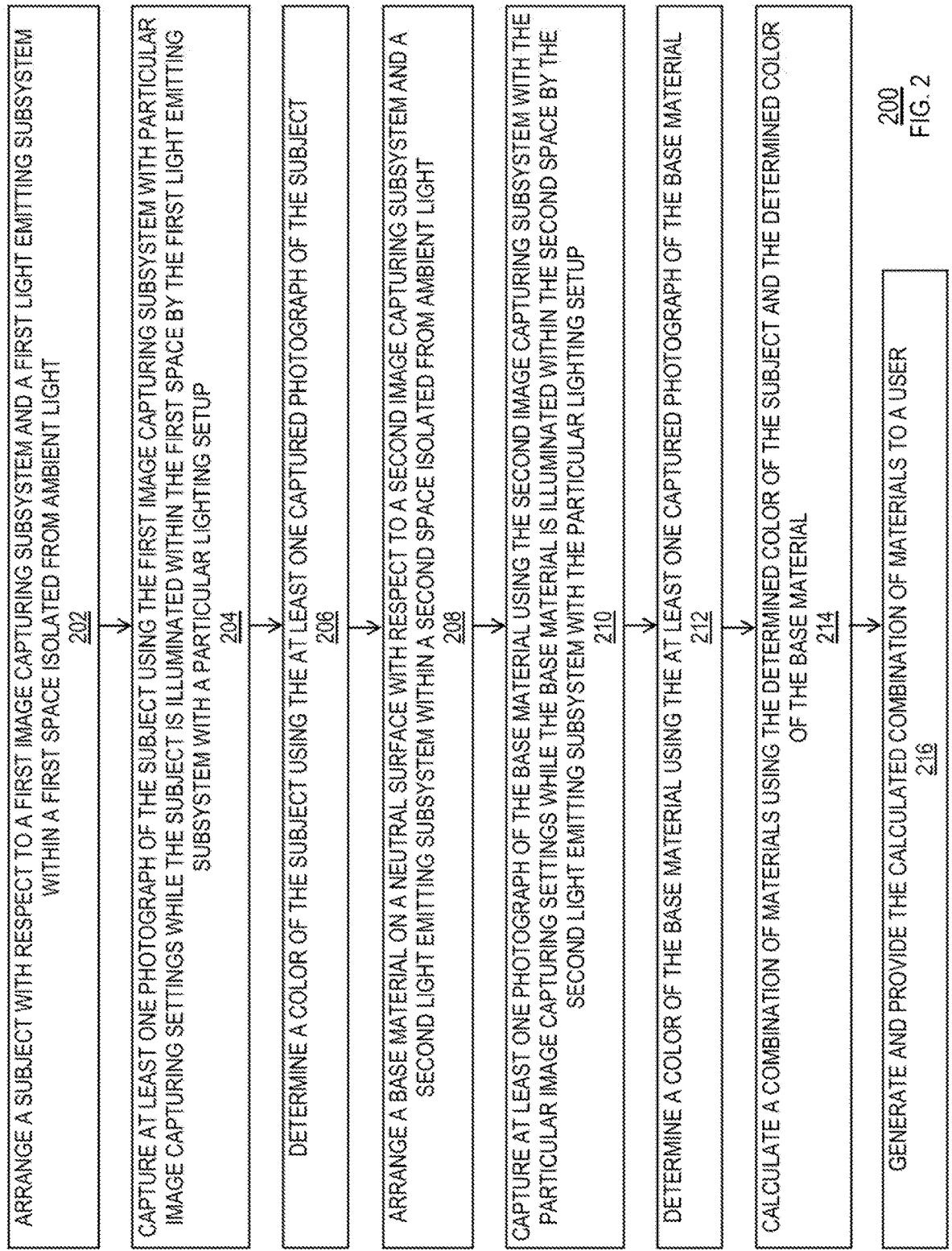
FIG. 2 is a flowchart of an illustrative process that may provide features of the color reproduction service of the disclosure.
Figure 3:
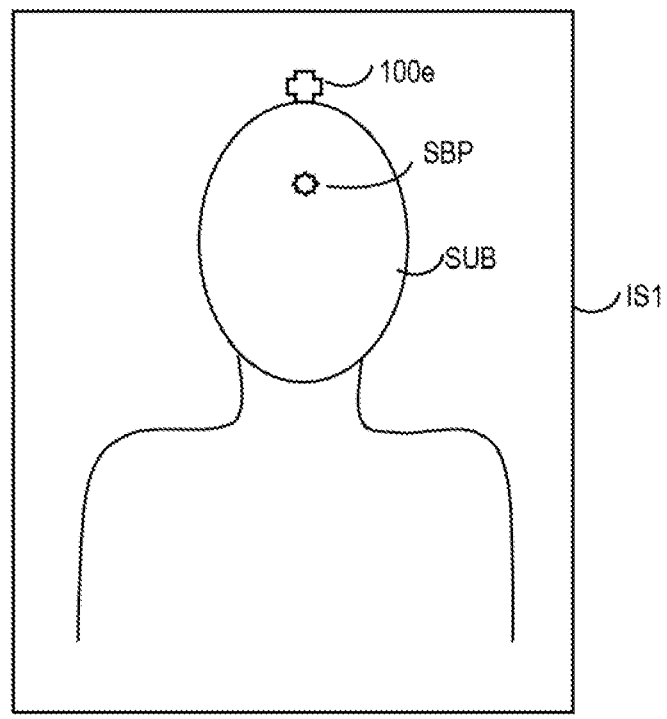
FIG. 3 is an illustrative photograph of a subject from the system of FIG. 1.
Figure 4:
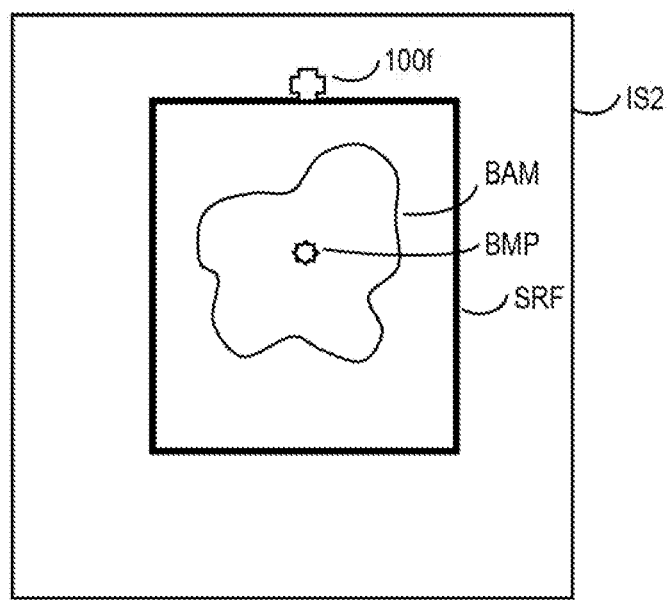
FIG. 4 is an illustrative photograph of a base material from the system of FIG. 1.

FIG. 1 shows a system 1 in which a color reproduction service may be facilitated amongst various entities, FIG. 1A shows further details with respect to a particular embodiment of a subsystem of system 1, FIG. 2 is a flowchart of an illustrative process that may provide features of the color reproduction service of the disclosure, FIG. 3 is an illustrative photograph of a subject from the system of FIG. 1, and FIG. 4 is an illustrative photograph of a base material from the system of FIG. 1.

FIG. 1 is a schematic view of an illustrative system 1 in which a color reproduction service may be facilitated amongst various entities. For example, as shown in FIG. 1, system 1 may include a color reproduction service ("CRS") subsystem 10, various subsystems 100 (e.g., one or more image capturing ("IC") subsystems, such as IC subsystems 100a and 100b, one or more light emitting ("LE") subsystems, such as LE subsystems 100c and 100d, and one or more light meter ("LM") subsystems, such as LM subsystems 100e and 100f), and at least one communications network 50 through which any two or more of subsystems 10 and 100 may communicate. CRS subsystem 10 may be operative to interact with any of the various subsystems 100 to provide a color reproduction service platform ("CRSP") that may facilitate various color reproduction services, including, but not limited to, color discovery, color profiling, and color creation services, that may be operative to discover accurate relative color on a physical surface and rapidly reproduce that color (e.g., with any suitable substance) on demand.

As shown in FIG. 1A, and as described in more detail below, CRS subsystem 10 may include a processor component 12, a memory component 13, a communications component 14, a sensor component 15, an input/output ("I/O") component 16, a power supply component 17, a data structure 19, and/or a bus 18 that may provide one or more wired or wireless communication links or paths for transferring data and/or power to, from, or between various other components of CRS subsystem 10. I/O component 16 may include at least one input component (e.g., a button, mouse, keyboard, microphone, input connector, etc.) to receive information from a user or environment of subsystem 10 and/or at least one output component (e.g., an audio speaker, video display, haptic component, output connector, base material mixer, etc.) to provide information or substance to a user of subsystem 10, such as a touch screen that may receive input information through a user's touch on a touch sensitive portion of a display screen and that may also provide visual information to a user via that same display screen and/or such as a base material output assembly that may be operative to make accessible to a user any suitable base material or combination of base materials (e.g., makeup material for application to the skin of a user). Memory 13 may include one or more storage mediums, including for example, a hard-drive, flash memory, permanent memory such as read-only memory ("ROM"), semi-permanent memory such as random access memory ("RAM"), any other suitable type of storage component, or any combination thereof. Communications component 14 may be provided to allow subsystem 10 to communicate with a communications component of one or more subsystems 100 or servers or other suitable entities of system 1 using any suitable communications protocol (e.g., via communications network 50). Communications component 14 can be operative to create or connect to a communications network for enabling such communication. Communications component 14 can provide wireless communications using any suitable short-range or long-range communications protocol, such as Wi-Fi (e.g., an 802.11 protocol), Bluetooth, radio frequency systems (e.g., 1200 MHz, 2.4 GHz, and 5.6 GHz communication systems), infrared, protocols used by wireless and cellular telephones and personal e-mail devices, or any other protocol supporting wireless communications. Communications component 14 can also be operative to connect to a wired communications network or directly to another data source wirelessly or via one or more wired connections or a combination thereof. Such communication may be over the internet or any suitable public and/or private network or combination of networks (e.g., one or more networks 50). Sensor 15 may be any suitable sensor that may be configured to sense any suitable data from an external environment of subsystem 10 or from within or internal to subsystem 10 (e.g., light data via a light sensor, audio data via an audio sensor, location-based data via a location-based sensor system (e.g., a global positioning system ("GPS")), etc.). Power supply 17 can include any suitable circuitry for receiving and/or generating power, and for providing such power to one or more of the other components of subsystem 10. Subsystem 10 may also be provided with a housing 11 that may at least partially enclose one or more of the components of subsystem 10 for protection from debris and other degrading forces external to subsystem 10. Each component of subsystem 10 may be included in the same housing 11 (e.g., as a single unitary device, such as a laptop computer or portable media device) and/or different components may be provided in different housings (e.g., a keyboard input component may be provided in a first housing that may be communicatively coupled to a processor component and a display output component that may be provided in a second housing, and/or multiple servers may be communicatively coupled to provide for a particular subsystem). In some embodiments, subsystem 10 may include other components not combined or included in those shown or several instances of one or more of the components shown.

Processor 12 may be used to run one or more applications, such as an application that may be provided as at least a part of one data structure 19 that may be accessible from memory 13 and/or from any other suitable source (e.g., from a subsystem 100 or from any suitable third party data source via an active internet connection or otherwise). Such an application data structure 19 may include, but is not limited to, one or more operating system applications, firmware applications, communication applications, internet browsing applications (e.g., for interacting with a website provided by the CRSP), CRS applications (e.g., a web application or a native application or a hybrid application or widget that may be at least partially produced by CRS subsystem 10 for enabling any subsystem 100 to interact with subsystem 10 and/or an online service of the CRSP via a CRS website or application or another entity's website or application), or any other suitable applications. For example, processor 12 may load an application data structure 19 as a user interface program to determine how instructions or data received via an input component of I/O component 16 or via communications component 14 or via sensor component 15 or via any other component of subsystem 10 may manipulate the way in which information may be stored and/or provided to a user via an output component of I/O component 16 and/or to any other subsystem via communications component 14. As one example, an application data structure 19 may provide a user or a communicatively coupled device or subsystem (e.g., any subsystem 100) with the ability to interact with a color reproduction service or the CRSP of system 1, where such an application 19 may be a third party application that may be running on subsystem 10 (e.g., an application (e.g., software and/or firmware) or at least one application program interface ("API") associated with the CRSP that may be loaded on or otherwise made accessible to subsystem 10 (e.g., via an application market)) and/or that may be accessed via an internet application or web browser running on subsystem 10 (e.g., processor 12) that may be pointed to a uniform resource locator ("URL") whose target or web resource may be at least partially managed by the CRSP. Subsystem 10 may be a portable media device (e.g., a smartphone), a laptop computer, a tablet computer, a desktop computer, an appliance, a wearable electronic device, a virtual reality device, a dongle device, at least one web or network server (e.g., for providing an online resource, such as a website or native online application or widget, for presentation on one or more other subsystems) with an interface for an administrator of such a server, and/or the like.

One, some, or each subsystem 100 of system 1 (e.g., one, some, or each one of subsystems 100a-100f) may include a housing that may be similar to housing 11, a processor component that may be similar to processor 12, a memory component that may be similar to memory component 13, a communications component that may be similar to communications component 14, a sensor component that may be similar to sensor component 15, an I/O component that may be similar to I/O component 16, a power supply component that may be similar to power supply component 17, and/or a bus that may be similar to bus 18. Moreover, one, some, or each subsystem 100 of system 1 may include one or more data sources or data structures or applications that may include any suitable data or one or more applications (e.g., any data structure that may be similar to data structure 19) for facilitating a color reproduction service or CRSP that may be provided by CRS subsystem 10 in conjunction with one or more subsystems 100.

CRS subsystem 10 and any subsystem 100 may be operative to communicate via communications network 50. Network 50 may be the internet or any other suitable network or any suitable wired or wireless direct connection, such that when intercoupled via network 50, any two subsystems of system 1 may be operative to communicate with one another (e.g., a subsystem 100 may access information (e.g., from a data structure 19 of CRS subsystem 10, as may be provided as a color reproduction service via processor 12 and communications component 14 of CRS subsystem 10) as if such information were stored locally at that subsystem 100 (e.g., in a memory component)).

System 1 may be utilized to provide a color reproduction service platform ("CRSP") that may facilitate various color reproduction services, including, but not limited to, color discovery, color profiling, and color creation services, which may be operative to discover accurate relative color on a physical surface and rapidly reproduce that color on demand with any suitable substance. FIG. 2 is a flowchart of an illustrative color reproduction process 200 that may be implemented by the CRSP and various subsystems of system 1. However, it is to be understood that process 200 may be implemented using any other suitable components or subsystems. Process 200 may provide a seamless user experience for efficiently and effectively reproducing a color of a subject in a base material form. To facilitate the following discussion regarding the operation of system 1 for color reproduction according to process 200 of FIG. 2, reference is made to various components of system 1 of the schematic diagrams of FIGS. 1 and 1A.

At operation 202 of process 200, a subject may be arranged with respect to a first image capturing subsystem and a first light emitting subsystem within a first space that may be isolated from ambient light. For example, as shown in FIG. 1, a subject SUB may be arranged with respect to IC subsystem 100*a* and LE subsystem 100*c* within a first space SP1 that may be isolated from any ambient light AL1 of a first environment EV1 by an isolation structure IS1. Isolation structure IS1 may be any suitable structure, such as any opaque material, that may be operative to prevent any ambient light AL1 from entering first space SP1, within which subject SUB and at least a portion of IC subsystem 100*a* and LE subsystem 100*c* may be positioned. Isolation structure IS1 may be operative to reflect no light or to reflect very little light. Alternatively, any reflectivity of light (e.g., light LT1 that may be emitted from LE subsystem 100*c*) by isolation structure IS1 may be determined and factored in to any processing by system 1 as a portion of the lighting setup (e.g., as a consistent source of bounce light).

Inside space SP1, a particular lighting setup may be provided using one or more LE subsystems 100*c* (e.g., any suitable light emitting diodes ("LEDs") and/or any other suitable illuminating sources) that may produce light LT1 of a specific color temperature and intensity when measured incidentally on subject SUB, for illuminating subject SUB with the particular lighting setup. The intensity of light may decrease with an increased distance of subject SUB from LE subsystem 100*c* and/or may increase with a decreased distance of subject SUB from LE subsystem 100*c*, whereby a consistent ability to produce light of a specific color temperature and intensity on the subject is critical, where the consistency may also be applicable to the distance and angle of the light emitting subsystem with respect to the subject.

One method of producing the desired consistent lighting setup on the subject may include positioning any suitable LM subsystem 100*e* (e.g., any suitable light meter or lux sensor or otherwise) next to (e.g., adjacent or directly in front of) any suitable portion SBP of subject SUB (e.g., the portion of a color that is to be determined), such that LM subsystem 100*e* may be operative to detect an incidental light intensity and/or color temperature of light LT1 at subject portion SBP, where such lighting setup detection (e.g., such detected light intensity and/or color temperature) may be utilized to adjust the lighting setup (e.g., light intensity and/or color temperature) of light LT1 emitted by LE subsystem 100*c* until the lighting setup matches a particular lighting setup. In some embodiments, any detected lighting setup information from LM subsystem 100*e* may be communicated to and received by CRS subsystem 10, which may analyze the information and then generate and communicate lighting setup adjustment information to LE subsystem 100*c* that may be operative to adjust the lighting setup (e.g., light intensity and/or color temperature) of light LT1 such that the lighting setup at portion SBP of subject SUB may be a particular lighting setup (e.g., as predefined by an application 19 of CRS subsystem 10). Alternatively, LM subsystem 100*e* and LE subsystem 100*c* may communicate directly with one another (e.g., not via CRS subsystem 10) to achieve the particular lighting setup. If LE subsystem 100*c* is stationary but subject SUB is not stationary, the subject can be guided into the position where LM subsystem 100*e* may detect the particular lighting setup (e.g., registers the specific color temperature and intensity) on the subject (e.g., at portion SBP of subject SUB). A combination of a mobile lighting device and a mobile subject may also work as long as portion SBP is illuminated by the particular lighting setup. Another method of ensuring that the subject has the correct lighting on its surface may include placing a lux sensor and/or color temperature sensor (e.g., LM subsystem 100*e*) at a consistent distance from LE subsystem 100*c* as well as at a consistent distance from the subject. LE subsystem 100*c* may increase or decrease its intensity (e.g., as may be measured in lumens, foot-candles, etc.) and/or may adjust its color temperature (e.g., as may be measured in Kelvins) until LM subsystem 100*e* may register the particular lighting setup at portion SBP of subject SUB. For example, a lighting source may be controlled by the same controller (e.g., iPad™ processor) that operates the camera and reads the LM data. An exemplary scenario may include a situation where voltage drops to the light source(s) and/or lux sensor(s) may result in a reading of 900 lux instead of 1,000 lux, whereby the controller may be operative to increase voltage to the light(s) until a desired 1,000 lux is read by the lux sensor(s). In the case of RGB common cathode LED light sources, the voltages to different color pins (e.g., of LE subsystem 100*c*) may be changed until the color temperature sensor (e.g., of LM subsystem 100*e*) shows a desired reading. A lighting setup may change based on the type of subject being analyzed (e.g., a ceiling light source may be used for a subject and/or base material that cannot rest vertically (e.g., a sedated subject or a powder base material)), where the configuration may change but the color temperature and/or light intensity may be the same for the different types of subjects. Another method may include using an LE subsystem 100*c* configured to utilize internal metrics (e.g., an internal LM subsystem) for adjusting light LT1 to provide consistent delivery of the desired color temperatures and intensities (e.g., a desired lighting setup). For all methods, when precision is critical, infrared distance sensors or the like can be used to guide the positioning of subject SUB within space SP1 to increase the accuracy of the lighting setup on the subject. The X, Y, and Z positioning of a subject in the space relative to the camera (e.g., IC subsystem 100*a*) and/or light sources (e.g., LE subsystem 100*c*) and/or light detectors (e.g., LM subsystem 100*e*) may be critical. If an iPad™ or other suitable device is being used, guideline overlays (e.g., a human face outline) in the camera preview can be used to increase positioning accuracy, where the outline may reduce error with respect to X-axis and Y-axis positioning, but may not be operative to reduce error with respect to Z-axis depth positioning. Correct depth position may be achieved using one or more infrared ("IR") distance sensors or other suitable mechanism. With no camera preview outline, three or more sensors may be needed. In some embodiments, a chin rest (or any other suitable physical structure that may functionally interact with a subject) may be provided within space SP1 for defining a specific position at which a face of a subject should be provided, where the chin rest may include a sensor or any other suitable component(s) that may be operative to be communicatively coupled to or otherwise detected by IC subsystem 100*a* and/or LE subsystem 100*c* and/or LM subsystem 100*e* to determine the position of the chin rest with respect to IC subsystem 100*a* and/or LE subsystem 100*c* and/or LM subsystem 100*e*. As another example, LM subsystem 100*e* may include one or more sensors (e.g., one or more IR distance sensors) that may be operative to determine a particular distance between the light meter sensor(s) of LM subsystem 100*e* and portion SBP of subject SUB, such that then the output light LT1 of LE subsystem 100*c* may be adjusted such that the particular color temperature and/or intensity may be detected at portion SBP by LM subsystem 100*e* while at the particular distance from portion SBP to achieve a more consistent color discovery process.

Next, at operation 204, while the particular lighting setup (e.g., particular color temperature and intensity) illuminates portion SBP of subject SUB within space SP1, at least one photograph (e.g., photograph 300 of FIG. 3) of at least one portion SBP of subject SUB (e.g., a portion of a surface of a face of a human user) may be captured by IC subsystem 100a with particular image capturing settings (e.g., consistently replicable settings, including, but not limited to, aperture, shutter speed, white balance (if present), and/or ISO settings (e.g., film speed and/or film or image sensor sensitivity settings). Sampling by taking multiple photos in quick succession at different pre-determined settings can be used to reduce color calculation variation. For example, for darker subjects, if the aperture of IC subsystem 100a (e.g., of a camera of IC subsystem 100a) is constant, the ISO of IC subsystem 100a may be higher and its shutter speed may be lower (e.g., to prevent data loss from pixels that may be captured and read as black). For lighter subjects, if the camera aperture is constant, the camera's ISO may be lower and its shutter speed may be higher to prevent color data loss, which may be known as clipping. At operation 206, the color (or color range) of a photo pixel or the average of the colors (or color ranges) over a number of pixels of the captured photograph(s) may then be used to determine the color (or color range) of portion SBP of subject SUB. A successive photograph approach may be useful in any suitable embodiments. For example, with one lighting setup, photographs can be taken at three different camera ISO's, such as at 50, 100, and 200. The photographs of the base materials taken at ISO 50 may be used to determine proportions necessary to mix the determined color of the subject with photographs taken at ISO 50. The photographs of the base materials taken at ISO 100 may be used to determine the proportions necessary to mix the color of the subject with photographs taken at ISO 100. The same may be done for ISO 200. The resulting proportions may be close at the different lighting settings because the material reflecting light is not changing and can be averaged across the three to reduce error. If one resulting proportion of base colors deviates greatly from the other two, it may signify data loss from clipping, and can automatically be dropped to reduce error. For example, a human subject with fair skin may be overexposed at ISO 200, so that photograph may be dropped because the pixels may read white and/or may contain no useable color information. A human subject with dark skin may be underexposed at ISO 50, so that photograph may be dropped because the pixels may read as black and/or may contain no useable color information. As another example, if there are two lighting setups, such as a more intense light at 5500K outdoor color temperature and a less intense light at 3200K indoor color temperature, the photographs of the base colors taken with the 5500K lighting setup may be used to determine proportions necessary to mix the determined color of the subject with photographs taken under the same 5500K lighting setup. The photographs of the base colors taken with the 3200K lighting setup may be used the determine the proportions necessary to mix the determined color of the subject with photographs taken under the 3200K lighting setup. The resulting proportions may also be comparable and can be averaged or weighted averaged depending on the final environment the mixed bases may be viewed in.

To translate this determined color of subject SUB to another material (e.g., a material of any suitable liquid, paint, powder, and/or the like), each one of any suitable number of differently colored base materials of the material may be photographed using the same particular lighting setup and the same particular image capturing settings as used to determine the color of portion SBP of subject SUB. For example, at operation 208 of process 200, a particular base material may be arranged with respect to a second image capturing subsystem and a second light emitting subsystem within a second space that may be isolated from ambient light. For example, as shown in FIG. 1, a particular base material BAM may be arranged with respect to IC subsystem 100b and LE subsystem 100d within a second space SP2 that may be isolated from any ambient light AL2 of a second environment EV2 by an isolation structure IS2. Isolation structure IS2 may be any suitable structure, such as any opaque material, that may be operative to prevent any ambient light AL2 from entering second space SP2, within which base material BAM and at least a portion of IC subsystem 100b and LE subsystem 100d may be positioned. Isolation structure IS2 may be operative to reflect no light or to reflect very little light. Alternatively, any reflectivity of light (e.g., light LT2 that may be emitted from LE subsystem 100d) by isolation structure IS2 may be determined and factored in to any processing by system 1 as a portion of the lighting setup (e.g., as a consistent source of bounce light).

Inside space SP2, the same particular lighting setup may be provided (e.g., as provided in space SP1) using one or more LE subsystems 100d (e.g., any suitable light emitting diodes ("LEDs") or other suitable illuminating sources) that may produce light LT2 of a specific color temperature and intensity when measured incidentally on base material BAM, for illuminating base material BAM with the particular lighting setup. Base material BAM may be provided in any suitable manner within space SP2, such as evenly spread along any suitable surface SRF (e.g., a color neutral and/or non-reflecting surface (e.g., a neutral grey sheet palette paper, a glass surface, a clear acrylic surface, etc.)). It is to be understood, however, that the space that may be used at operations 208 and 210 may, in some embodiments, be the same space that may be used at operations 202 and 204. While in other embodiments, the space that may be used at operations 208 and 210 may be different than the space that may be used at operations 202 and 204 (e.g., images of base materials may be captured in a first location while an image of a subject may be captured in a different location using the same or different apparatus).

One method of producing the desired consistent lighting setup on the base material may include positioning any suitable LM subsystem 100f (e.g., any suitable light meter or lux sensor or otherwise) next to (e.g., adjacent) any suitable portion BMP of base material BAM (e.g., the portion of a color that is to be determined), such that LM subsystem 100f may be operative to detect an incidental light intensity and/or color temperature of light LT2 at base material portion BMP, where such lighting setup detection (e.g., such detected light intensity and/or color temperature) may be utilized to adjust the lighting setup (e.g., light intensity and/or color temperature) of light LT2 emitted by LE subsystem 100d until the lighting setup matches a particular lighting setup (e.g., the same particular lighting setup described above on subject portion SBP within space SP1). In some embodiments, any detected lighting setup information from LM subsystem 100f may be communicated to and received by CRS subsystem 10, which may analyze the information and then generate and communicate lighting setup adjustment information to LE subsystem 100d that may be operative to adjust the lighting setup (e.g., light intensity and/or color temperature) of light LT2 such that the lighting setup at portion BMP of base material BAM may be the particular lighting setup (e.g., as predefined by an application 19 of CRS subsystem 10). Alternatively, LM subsystem 100*f* and LE subsystem 100*d* may communicate directly with one another to achieve the particular lighting setup. Another method of ensuring that the base material has the correct lighting on its surface may include placing a lux sensor and/or color temperature sensor (e.g., LM subsystem 100*f*) at a consistent distance from LE subsystem 100*d* as well as at a consistent distance from base material BAM. LE subsystem 100*d* may increase or decrease its intensity (e.g., as may be measured in lumens, foot-candles, etc.) and/or may adjust its color temperature (e.g., as may be measured in Kelvins) until LM subsystem 100*f* may register the particular lighting setup at portion BMP of base material BAM. Another method may include using an LE subsystem 100*d* configured to utilize internal metrics (e.g., an internal LM subsystem) for adjusting light LT2 to provide consistent delivery of the desired color temperatures and intensities (e.g., the desired lighting setup). For all methods, when precision is critical, infrared distance sensors or the like can be used to guide the positioning of base material BAM within space SP2 to increase the accuracy of the lighting setup on the base material.

Next, at operation 210, while the particular lighting setup (e.g., particular color temperature and intensity) illuminates portion BMP of base material BAM within space SP2, at least one photograph (e.g., photograph 400 of FIG. 4) of at least portion BMP of base material BAM (e.g., a portion of a particular makeup base material applied with an appropriate application thickness to surface SRF) may be captured by IC subsystem 100*b* with particular image capturing settings (e.g., the same particular image capturing settings used by IC subsystem 100*a* at operation 204). Sampling by taking multiple photos in quick succession at different pre-determined settings can be used to reduce color calculation variation. For example, for darker base materials, if the aperture of IC subsystem 100*b* (e.g., of a camera of IC subsystem 100*b*) is constant, the ISO of IC subsystem 100*b* may be higher and its shutter speed may be lower (e.g., to prevent data loss from pixels that may be read as black). For lighter base materials, if the camera aperture is constant, the camera's ISO may be lower and its shutter speed may be higher to prevent color data loss, which may be known as clipping. At operation 212, the color (or color range) of a photo pixel or the average of the colors (or color ranges) over a number of pixels of the captured photograph(s) of base material BAM may then be used to determine the color (or color range) of portion BMP of base material BAM. In some embodiments, space SP1 may be the same as space SP2 or may be different than space SP2. In some embodiments, structure IS1 may be the same as structure IS2 or may be different than structure IS2. In some embodiments, IC subsystem 100*a* may be the same as IC subsystem 100*b* or may be different than IC subsystem 100*b*. In some embodiments, LE subsystem 100*c* may be the same as LE subsystem 100*d* or may be different than LE subsystem 100*d*. In some embodiments, LM subsystem 100*e* may be the same as LM subsystem 100*f* or may be different than LM subsystem 100*f*. Operations 202-206 may be performed before, during, or after operations 208-212. Multiple distinct iterations of operations 208-212 may be carried out for each one of any suitable number of different base materials (e.g., any suitable number (e.g., 22-28) of base materials of an off the shelf foundation line), such that a color of each different base material may be determined using the particular image capturing settings and the particular lighting setup.

Use of multiple pre-determined lighting setups set at varying color temperatures and intensities to determine the color of the subject and to determine the color of a base material can increase the accuracy of the color determination and translation. Ranges of color instead of an average can also be used to determine colors within a tolerance.

At operation 214, a particular combination of materials may be calculated using the determined color of the subject and the determined color of at least two base materials (e.g., the color of each one of any two or more base materials determined at any two or more iterations of operations 208-212). The particular combination of materials may be calculated such that the color of the combination may match the determined color of the subject (e.g., match or come as close to matching as possible given the available base materials). The particular combination of materials may include any suitable first amount of a first base material determined to have a first color at a first iteration of operations 208-212 and any suitable second amount of a second base material determined to have a second color at a second iteration of operations 208-212. It is to be understood that any suitable number of base materials may be used at respective iterations of operations 208-212 and all such base materials or any suitable subset of such base materials may be used at operation 214 and/or operation 216 (e.g., any two or more base materials of any three or more available base materials). In some embodiments, any captured photograph of subject SUB may be communicated from IC subsystem 100*a* to CRS subsystem 10 and any captured photograph of each base material (e.g., base material BAM) may be communicated from IC subsystem 100*b* to CRS subsystem 10, and then CRS subsystem 10 may be operative to calculate the particular color of the subject and each base material using such captured photographs and to determine the particular combination of base materials using such calculated colors (e.g., using any suitable CRS application 19). Then, at operation 216, the calculated combination of materials may be generated and provided to a user. For example, CRS subsystem 10 may be operative to combine two or more available base materials pursuant to the calculated combination of materials in order to provide an end user with the combined material, which may have the same color as portion SBP of subject SUB (e.g., by mixing together a first amount of a first liquid makeup foundation base material and a second amount of a second liquid makeup foundation base material to create a material combination for use by subject SUB). System 1 may be used to determine the maximum range of colors supported by a set of colors of a set of base materials for a particular type of material (e.g., makeup foundation), thereby allowing producers of such material to increase or decrease the number of colors of base materials made available to system 1 for mixing depending on the application. Current products can be profiled and used for customization without disrupting supply chains.

Therefore, system 1 may be used to reduce or remove ambient light, use one or more controlled light sources to create light of a precise color temperature and intensity on a subject, capture at least one image of the illuminated subject using pre-determined camera settings, determine the relative color of the subject from the captured image(s), and translate that color value to a combination of base materials with colors previously determined in a similar manner to that of the subject. The combination of base materials may be provided as a mixed custom color liquid foundation. Operations 202-206, 214, and 216 may be completed in an efficient and convenient amount of time for an end user (e.g., subject SUB), such as under 3 minutes or potentially under 1 minute, where one or more sets of operations 208-212 may be completed concurrently or before operations 202-206, 214, and/or 216. In some embodiments, a portable electronic device, such as an iPad™ by Apple Inc., may be used to provide IC subsystem 100a (e.g., with a camera of the device) and/or a CRSP interface for a user (e.g., with a touch screen UI for subject SUB or another end user), where the interface may be operative to instruct subject SUB how to position itself within space SP1 and/or to display at least one photograph 300 of subject SUB that may be interacted with by a user for selecting a portion of that photograph (e.g. a portion indicative of portion SBP of subject SUB) to be used for determining a color of the subject that may then be used for calculating a color of material to be generated by a combination of one or more base materials. LE subsystem 100c may be provided by a light emitting component of that same electronic device (e.g., a sustained flash or light of an iPad™) or by a separate array of LEDs that may be positioned above the device providing IC subsystem 100a (e.g., a ring of LEDs that may be provided around the periphery of the electronic device housing (e.g., an iPad™), which may provide for more even lighting (e.g., from forehead to neck) of the subject). Similarly, LM subsystem 100e may be provided by a light detecting component of that same electronic device (e.g., one or more IR sensors of an iPad™) or by a separate IR sensor (or sensors) and/or light meter that may be positioned adjacent the device providing IC subsystem 100a and/or the device providing LE subsystem 100c. A base material output assembly may be provided by a distinct subsystem that may be communicatively coupled to such a device (e.g., to an iPad™ via network 50). Alternatively, two or more or all of IC subsystem 100a, LE subsystem 100c, LM subsystem 100e, and the base material output assembly may be provided by a single unitary device or structure.

It is understood that the operations shown in process 200 of FIG. 2 are only illustrative and that existing operations may be modified or omitted, additional operations may be added, and the order of certain operations may be altered.

One, some, or all of the processes described with respect to FIGS. 1-4 may each be implemented by software, but may also be implemented in hardware, firmware, or any combination of software, hardware, and firmware. Instructions for performing these processes may also be embodied as machine- or computer-readable code recorded on a machine- or computer-readable medium. In some embodiments, the computer-readable medium may be a non-transitory computer-readable medium. Examples of such a non-transitory computer-readable medium include but are not limited to a read-only memory, a random-access memory, a flash memory, a CD-ROM, a DVD, a magnetic tape, a removable memory card, and a data storage device (e.g., memory 13 and/or data structure 19 of FIG. 1A). In other embodiments, the computer-readable medium may be a transitory computer-readable medium. In such embodiments, the transitory computer-readable medium can be distributed over network-coupled computer systems so that the computer-readable code may be stored and executed in a distributed fashion. For example, such a transitory computer-readable medium may be communicated from CRS subsystem 10 to a subsystem 100, from a subsystem 100 to CRS subsystem 10, and/or from one subsystem 100 to another subsystem 100 using any suitable communications protocol (e.g., the computer-readable medium may be communicated to a subsystem 100 via communications component 14 (e.g., as at least a portion of a data structure 19)). Such a transitory computer-readable medium may embody computer-readable code, instructions, data structures, program modules, or other data in a modulated data signal, such as a carrier wave or other transport mechanism, and may include any information delivery media. A modulated data signal may be a signal that has one or more of its characteristics set or changed in such a manner as to encode information in the signal.

It is to be understood that any, each, or at least one module or component or subsystem of the disclosure may be provided as a software construct, firmware construct, one or more hardware components, or a combination thereof. For example, any, each, or at least one module or component or subsystem of system 1 may be described in the general context of computer-executable instructions, such as program modules, that may be executed by one or more computers or other devices. Generally, a program module may include one or more routines, programs, objects, components, and/or data structures that may perform one or more particular tasks or that may implement one or more particular abstract data types. It is also to be understood that the number, configuration, functionality, and interconnection of the modules and components and subsystems of system 1 are only illustrative, and that the number, configuration, functionality, and interconnection of existing modules, components, and/or subsystems may be modified or omitted, additional modules, components, and/or subsystems may be added, and the interconnection of certain modules, components, and/or subsystems may be altered. It is also to be understood that any two or more of subsystems 10 and 100a-100f may be the same subsystem or provided by a single electronic device. For example, a single iPad™ may be used to provide any two or more of subsystems 10 and 100a-100f.

While there have been described systems, methods, and computer-readable media for a color reproduction service, it is to be understood that many changes may be made therein without departing from the spirit and scope of the subject matter described herein in any way. Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

Therefore, those skilled in the art will appreciate that the invention can be practiced by other than the described embodiments, which are presented for purposes of illustration rather than of limitation.

What is claimed is:

1. A method for defining a mixture, the method comprising:
    capturing a photograph of a first base material using a first image capturing subsystem with first image capturing settings while the first base material is illuminated within a first space by a first light emitting subsystem with a first lighting setup;
    determining a color of the first base material using the captured photograph of the first base material;
    capturing a photograph of a second base material using a second image capturing subsystem with second image capturing settings while the second base material is illuminated within a second space by a second light emitting subsystem with a second lighting setup;
    determining a color of the second base material using the captured photograph of the second base material, wherein the determined color of the second base material is different than the determined color of the first base material;

capturing a photograph of a subject using a third image capturing subsystem with third image capturing settings while the subject is illuminated within a third space by a third light emitting subsystem with a third lighting setup;

determining a color of the subject using the captured photograph of the subject, wherein the determined color of the subject is different than the determined color of the first base material, and wherein the determined color of the subject is different than the determined color of the second base material; and using the determined color of the first base material and the determined color of the second base material and the determined color of the subject, determining a combination comprising a first amount of the first base material and a second amount of the second base material such that a color of the determined combination matches the determined color of the subject.

2. The method of claim 1, further comprising, after determining the combination, providing the first amount of the first base material and the second amount of the second base material to the subject.

3. The method of claim 1, wherein the first image capturing subsystem and the second image capturing subsystem are the same image capturing subsystem.

4. The method of claim 1, wherein the first image capturing settings and the second image capturing settings are the same image capturing settings.

5. The method of claim 1, wherein the first space and the second space are the same space.

6. The method of claim 1, wherein the first light emitting subsystem and the second light emitting subsystem are the same light emitting subsystem.

7. The method of claim 1, wherein the first lighting setup and the second lighting setup are the same lighting setup.

8. The method of claim 1, wherein:
the first lighting setup comprises light of a first color temperature and a first intensity;
the second lighting setup comprises light of a second color temperature and a second intensity;
the second color temperature is the same as the first color temperature; and
the second intensity is the same as the first intensity.

9. The method of claim 1, wherein:
the first space is isolated from any ambient light during the capturing of the photograph of the first base material;
the second space is isolated from any ambient light during the capturing of the photograph of the second base material; and
the third space is isolated from any ambient light during the capturing of the photograph of the subject.

10. The method of claim 1, wherein the first image capturing settings and the second image capturing settings share at least one type of the following types of image capturing settings:
aperture;
shutter speed;
white balance; and
image sensor sensitivity.

11. The method of claim 1, wherein:
the first image capturing subsystem and the second image capturing subsystem are the same image capturing subsystem;
the first image capturing settings and the second image capturing settings are the same image capturing settings;
the first space and the second space are the same space;
the first light emitting subsystem and the second light emitting subsystem are the same light emitting subsystem; and
the first lighting setup and the second lighting setup are the same lighting setup.

12. The method of claim 1, wherein:
the first space and the third space are not the same space; and
the first light emitting subsystem and the third light emitting subsystem are not the same light emitting subsystem.

13. The method of claim 12, wherein the first lighting setup and the third lighting setup are the same lighting setup.

14. The method of claim 12, wherein the first image capturing subsystem and the third image capturing subsystem are not the same image capturing subsystem.

15. The method of claim 14, wherein the first image capturing settings and the third image capturing settings are the same image capturing settings.

16. The method of claim 1, wherein:
the first image capturing subsystem and the second image capturing subsystem are the same image capturing subsystem;
the first image capturing settings and the second image capturing settings are the same image capturing settings;
the first space and the second space are the same space;
the first light emitting subsystem and the second light emitting subsystem are the same light emitting subsystem;
the first lighting setup and the second lighting setup are the same lighting setup;
the first space and the third space are not the same space;
the first lighting setup and the third lighting setup are the same lighting setup; and
the first image capturing settings and the third image capturing settings are the same image capturing settings.

17. The method of claim 16, wherein:
the first image capturing subsystem and the third image capturing subsystem are not the same image capturing subsystem; and
the first light emitting subsystem and the third light emitting subsystem are not the same light emitting subsystem.

18. The method of claim 1, wherein:
the first base material is a first liquid makeup foundation base material;
the second base material is a second liquid makeup foundation base material; and
the subject is a portion of a user's face.

19. A system comprising:
an image capturing ("IC") subsystem;
a light emitting ("LE") subsystem;
a light meter ("LM") subsystem; and
a color reproduction service ("CRS") subsystem communicatively coupled to the IC subsystem and the LE subsystem and the LM subsystem and comprising a processor operative to:
capture an image of a first base material using the IC subsystem with first image capturing settings when the first base material is determined by the LM subsystem to be illuminated by the LE subsystem with a first lighting setup;
determine a color of the first base material using the captured image of the first base material;

capture an image of a second base material using the IC subsystem with the first image capturing settings when the second base material is determined by the LM subsystem to be illuminated by the LE subsystem with the first lighting setup;

determine a color of the second base material using the captured image of the second base material;

capture an image of a subject using the IC subsystem with the first image capturing settings when the subject is determined by the LM subsystem to be illuminated by the LE subsystem with the first lighting setup;

determine a color of the subject using the captured image of the subject; and based on the determined color of each one of the first base material, the second base material, and the subject, calculate a mixture comprising a first amount of the first base material and a second amount of the second base material such that a color of the calculated mixture is the same as the determined color of the subject.

20. A non-transitory computer-readable storage medium storing at least one program, the at least one program comprising instructions, which when executed by an electronic device, cause the electronic device to:

obtain an image of a first base material, wherein the image of the first base material was captured using first image capturing settings while the first base material was illuminated with a first lighting setup;

obtain an image of a second base material, wherein the image of the second base material was captured using first image capturing settings while the second base material was illuminated with the first lighting setup;

obtain an image of a subject, wherein the image of the subject was captured using first image capturing settings while the subject was illuminated with the first lighting setup;

determine a color of the first base material using the obtained image of the first base material;

determine a color of the second base material using the obtained image of the second base material;

determine a color of the subject using the obtained image of the subject; and calculate, using the determined color of each one of the first base material, the second base material, and the subject, a mixture comprising a first amount of the first base material and a second amount of the second base material such that a color of the calculated mixture is the same as the determined color of the subject.

* * * * *